United States Patent [19]
Nojiri et al.

[11] Patent Number: 6,030,188
[45] Date of Patent: *Feb. 29, 2000

[54] CENTRIFUGAL BLOOD PUMP ASSEMBLY HAVING MAGNETIC MATERIAL EMBEDDED IN IMPELLER VANES

[75] Inventors: Toshihiko Nojiri, Kanagawa-ken; Tsugito Nakazeki, Shizuoka-ken, both of Japan

[73] Assignees: Terumo Kabushiki Kaisha, Tokyo; NTN Corporation, Osaka, both of Japan

[*] Notice: This patent issued on a continued prosecution application filed under 37 CFR 1.53(d), and is subject to the twenty year patent term provisions of 35 U.S.C. 154(a)(2).

[21] Appl. No.: 08/863,600

[22] Filed: May 27, 1997

[30] Foreign Application Priority Data

May 28, 1996 [JP] Japan ..................................... 8-157711

[51] Int. Cl.[7] ..................................... F04B 17/00
[52] U.S. Cl. .......................... 417/420; 417/365; 415/900
[58] Field of Search ..................................... 417/420, 365; 415/900, 14; 416/223 B, 179, 185, 186 R

[56] References Cited

U.S. PATENT DOCUMENTS

| | | |
|---|---|---|
| 3,107,310 | 10/1963 | Carriere et al. . |
| 3,139,832 | 7/1964 | Saunders . |
| 3,487,784 | 1/1970 | Rafferty et al. . |
| 3,647,324 | 3/1972 | Rafferty et al. .......................... 416/179 |
| 3,864,055 | 2/1975 | Kletschka et al. . |
| 3,957,389 | 5/1976 | Rafferty et al. . |
| 3,970,408 | 7/1976 | Rafferty et al. . |
| 4,981,417 | 1/1991 | Arbeus ..................................... 416/179 |
| 5,112,202 | 5/1992 | Oshima et al. .......................... 415/900 |
| 5,180,280 | 1/1993 | Honda .................................. 416/223 B |
| 5,658,136 | 8/1997 | Mendler ................................. 417/420 |
| 5,695,471 | 12/1997 | Wampler ............................. 417/423.7 |
| 5,947,703 | 9/1999 | Nojiri et al. ............................. 417/420 |

FOREIGN PATENT DOCUMENTS

| | | |
|---|---|---|
| 1 051 123 | 5/1959 | Germany . |
| 57-23114 | 5/1982 | Japan ..................................... 415/900 |
| 62237093 | 10/1987 | Japan ..................................... 417/420 |
| 01257792 | 10/1989 | Japan . |
| 82/03176 | 9/1982 | WIPO .................................. 415/900 |

OTHER PUBLICATIONS

T. Akamatsu et al., "Recent Studies of the Centrifugal Blood Pump with a Magnetically Suspended Impeller", *Artif Organs.*, vol. 19, No. 7, 1995, pp. 631–634.

Garay, Paul; Pump Application Desk Book; pp. 66–67, Jan. 1996.

*Primary Examiner*—Timothy S. Thorpe
*Assistant Examiner*—Cheryl J. Tyler
*Attorney, Agent, or Firm*—Burns, Doane, Swecker & Mathis, LLP

[57] ABSTRACT

A centrifugal fluid pump assembly includes a housing having fluid inlet and outlet ports and an impeller having magnetic pieces disposed therein and accommodated for rotation in the housing for feeding the fluid, typically blood by a centrifugal force developed during rotation. A rotational torque generating mechanism including a rotor having magnets for attracting the magnetic pieces in the impeller and a motor for rotating the rotor serves to impart a rotational torque to the impeller in a non-contact relationship for thereby rotating the impeller. The impeller has vanes which define radially outwardly extending fluid passages therebetween. The magnetic pieces are embedded in the vanes.

16 Claims, 9 Drawing Sheets

F I G. 2
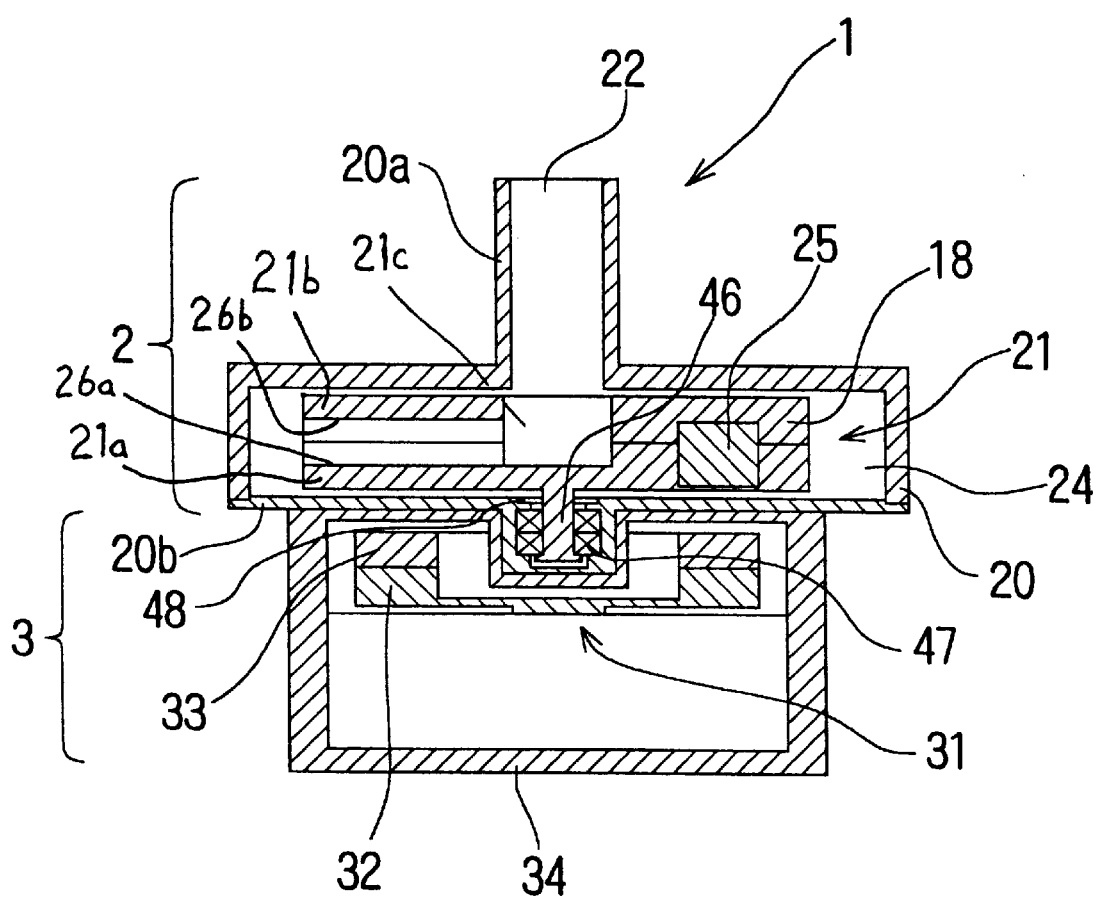

CENTRIFUGAL BLOOD PUMP ASSEMBLY HAVING MAGNETIC MATERIAL EMBEDDED IN IMPELLER VANES

BACKGROUND OF THE INVENTION

This invention relates to a centrifugal fluid pump assembly for pumping a medical fluid, typically blood.

In modern medical treatment, centrifugal blood pumps are often used in artificial heart/lung units for extracorporeal blood circulation. Centrifugal pumps of the magnetic coupling type wherein a driving torque from an external motor is transmitted to the impeller through magnetic coupling are commonly used because the physical communication between the blood chamber of the pump and the exterior can be completely excluded to prevent invasion of bacteria.

In general, centrifugal blood pumps include a housing having a blood inlet port and a blood outlet port and an impeller accommodated for rotation in the housing for feeding blood by a centrifugal force developed during rotation. The impeller having magnetic pieces of permanent magnet disposed therein is rotated by a rotational torque generating mechanism which includes a rotor having magnets for attracting the magnetic pieces of the impeller and a motor for rotating the rotor. The magnetic pieces of permanent magnet in the impeller are generally located within a shroud of the impeller as shown in FIG. 3 of Japanese Pat. Publication (JP-B) No. 23114/1982 and U. S. Pat. 5,112,202. JP-B 23114/1982 discloses in FIG. 7 another embodiment wherein magnetic pieces are located in a magnet chamber separately formed outside the blood chamber.

In the latter embodiment wherein magnets are received in the magnet chamber as shown in FIG. 7 of JP-B 23114/1982, a seal is provided between the blood and magnet chambers for preventing blood from penetrating into the magnet chamber. If a negative pressure develops within the pump as a result of accidental blockage of a portion of the circuit upstream of the pump, the direction of the pressure load applied to the seal is reversed, increasing the risk that air in the magnet chamber be sucked into the blood chamber.

The centrifugal pumps wherein magnets are located in the impeller shroud are substantially free of such a risk because the volume of air in the bearing chamber is very small. However, the height of the blood pump chamber is increased by the height of magnets to increase the amount of blood with which the chamber is filled. It is also known for centrifugal pumps that a radial imbalance of pressure distribution creates a radial thrust which is in proportion to the radially projected area of the impeller. Therefore, centrifugal pumps of this type have the problem that an increase of the axial height of the impeller leads to an increase of the radially projected area of the impeller which in turn, increases the radial thrust developed by a radial imbalance of pressure distribution, which in turn, increases the radial load on the bearing.

SUMMARY OF THE INVENTION

Therefore, an object of the invention is to provide a novel and improved centrifugal fluid pump assembly of the magnetic coupling type which does not carry air into the blood chamber or increase the blood fill amount and the radial thrust of the impeller.

According to a first aspect of the invention, there is provided a centrifugal fluid pump assembly comprising a housing having an inlet port and an outlet port for fluid and adapted to receive fluid therein; an impeller having a magnetic material disposed therein and accommodated for rotation in the housing for feeding the fluid by a centrifugal force developed during rotation; and a rotational torque generating mechanism comprising a rotor having a magnet for attracting the magnetic material in the impeller and a motor for rotating the rotor, the rotational torque generating mechanism serving to impart a rotational torque to the impeller in a non-contact relationship for thereby rotating the impeller. The impeller has a plurality of vanes which define therebetween a corresponding plurality of fluid passages extending from the center to the outer periphery of the impeller. The magnetic material is disposed in the vane.

According to a second aspect of the invention, there is provided a centrifugal fluid pump assembly comprising a centrifugal fluid pump section comprising a housing having an inlet port and an outlet port for fluid and adapted to receive fluid therein and an impeller having a magnetic material disposed therein and accommodated for rotation in the housing for feeding the fluid by a centrifugal force developed during rotation; and a rotational torque generating section comprising a rotor having a magnet for attracting the magnetic material in the impeller and a motor for rotating the rotor, the rotational torque generating section serving to impart a rotational torque to the impeller in a non-contact relationship. The impeller has a plurality of vanes which define therebetween a corresponding plurality of fluid passages extending from the center to the outer periphery of the impeller. The magnetic material is disposed in the vane.

According to a third aspect of the invention, there is provided a centrifugal fluid pump assembly comprising a centrifugal fluid pump comprising a housing having an inlet port and an outlet port for fluid and adapted to receive fluid therein and an impeller having a magnetic material disposed therein and accommodated for rotation in the housing for feeding the fluid by a centrifugal force developed during rotation; controlled magnetic bearing means for magnetically supporting the impeller; and uncontrolled magnetic bearing means for magnetically supporting the impeller, the uncontrolled magnetic bearing means comprising a rotor having a magnet for attracting the magnetic material in the impeller and a motor for rotating the rotor. The controlled magnetic bearing means and the uncontrolled magnetic bearing means cooperate such that the impeller rotates while it is held in position within the housing. The impeller has a plurality of vanes which define therebetween a corresponding plurality of fluid passages extending from the center to the outer periphery of the impeller. The magnetic material is disposed in the vane. In one preferred embodiment of the third aspect, the impeller further includes a magnetic member for constituting a magnetic bearing with the controlled magnetic bearing means, and the controlled magnetic bearing means includes a fixed electromagnet for attracting the magnetic member of the impeller and a position sensor for detecting the position of the magnetic member of the impeller.

In one preferred embodiment of the first to third aspects, plural pieces of magnetic material are disposed in plural vanes, more preferably all vanes. Also preferably the fluid passages in the impeller have a cross-sectional area which is substantially constant or declining in a fluid flow direction, and the fluid passages in the impeller extend straight.

Most often, the centrifugal fluid pump assembly is a centrifugal blood pump assembly.

BRIEF DESCRIPTION OF THE DRAWINGS

The above and other objects, features and advantages of the invention will be better understood by reading the following description, taken in conjunction with the accompanying drawings.

FIGS. 1 and 2 illustrate a centrifugal fluid pump assembly according to a first embodiment of the invention. FIG. 1 is a horizontal cross-sectional view of the impeller therein. FIG. 2 is a vertical cross-sectional view of the pump assembly, with only the impeller being cut along a curved dot-and-dash line in FIG. 1.

FIG. 3 is a horizontal cross-sectional view of the impeller therein FIG. 4 is a vertical crossectional view of the pump assembly, with only the impeller being cut along a curved dot-and-dash line in FIG. 3.

FIG. 5 is a horizontal cross-sectional view of the impeller therein FIG. 6 is a vertical cross-sectional view of the pump assembly, with only the impeller being cut along a curved dot-and-dash line in FIG. 5.

FIG. 7 is a horizontal cross-sectional view of the impeller therein. FIG. 8 is a vertical cross-sectional view of the pump assembly, with only the impeller being cut along a curved dot-and-dash line in FIG. 7.

DESCRIPTION OF THE PREFERRED EMBODIMENTS

Several embodiments of the centrifugal fluid pump assembly according to the invention are described with reference to the accompanying drawings.

Figure 1:
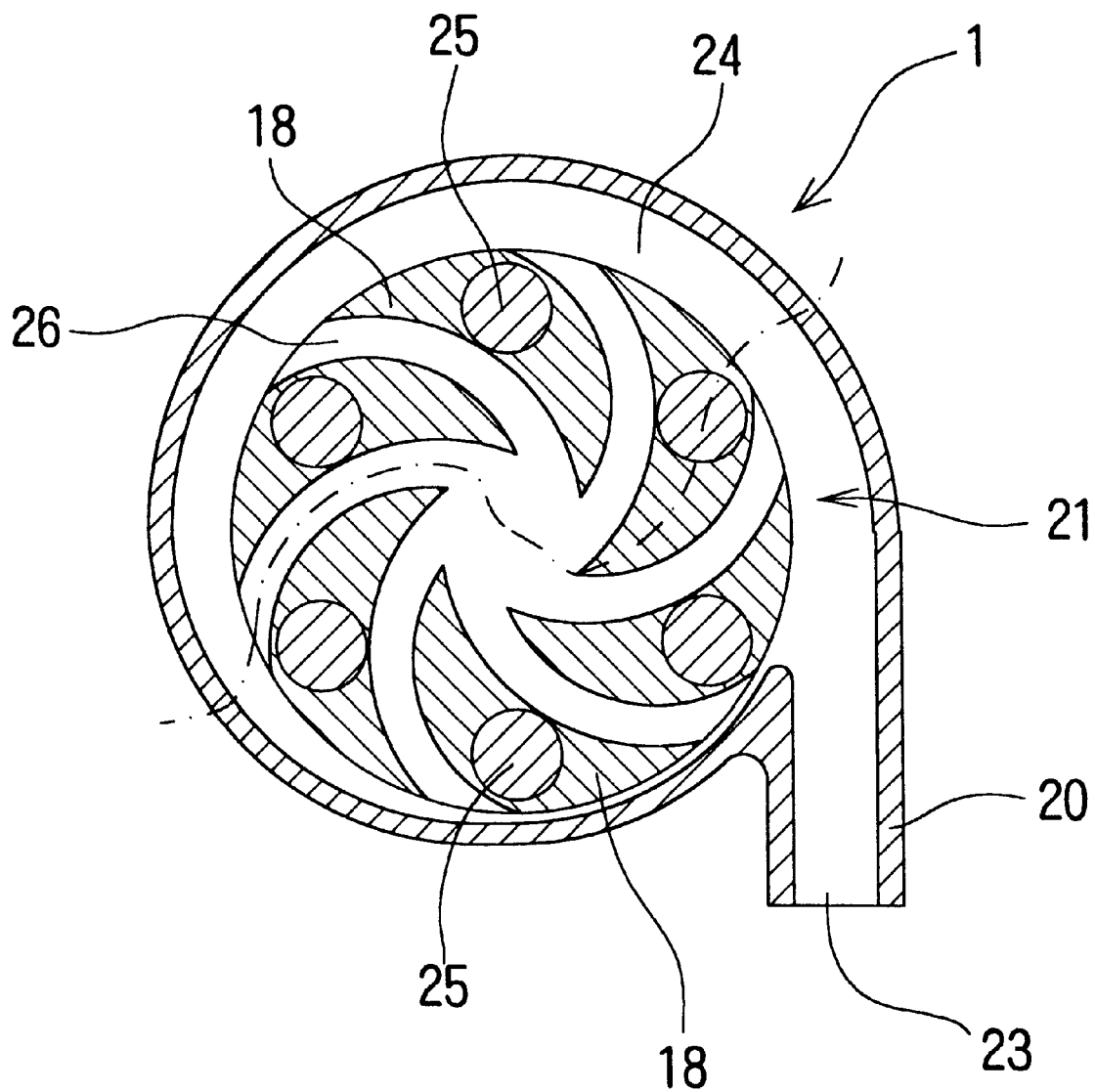

First referring to FIGS. 1 and 2, a centrifugal fluid pump assembly according to a first embodiment of the invention is described. FIG. 1 is a horizontal cross-sectional view of the impeller therein. FIG. 2 is a vertical cross-sectional view of the pump assembly. In FIG. 2, only the impeller is cut along a curved dot-and-dash line in FIG. 1.

The centrifugal fluid pump assembly of the invention, which is generally designated at 1, includes a housing 20 having a fluid inlet port 22 and a fluid outlet port 23 and adapted to receive a fluid, typically blood therein and an impeller 21 having a magnetic material 25 disposed therein and accommodated for rotation in the housing 20 for feeding the fluid by a centrifugal force developed during rotation. The pump assembly 1 further comprises a rotational torque generating mechanism including a rotor 31 having a magnet 33 for magnetically attracting the magnetic material 25 in the impeller 21 and a motor, not shown, for rotating the rotor 31. The rotational torque generating mechanism serves to impart a rotational torque to the impeller 21 in a non-contact relationship for thereby rotating the impeller 21. The impeller 21 has a plurality of vanes 18 which define therebetween a corresponding plurality of fluid passages 26 extending from the center to the outer periphery of the impeller 21. The magnetic material 25 is disposed in the vane 18.

Since the fluid pump assembly of the invention is typically applied as a blood pump, the following description refers to its embodiment as a blood pump.

The centrifugal fluid pump assembly 1 according to the embodiment illustrated in FIGS. 1 and 2 includes a blood pump section 2 and an impeller rotation torque generating section 3.

The blood pump section 2 includes a generally cylindrical housing 20 having a blood inlet port 22 and a blood outlet port 23 and defining therein a generally cylindrical blood chamber 24 in fluid communication with the inlet and outlet ports 22 and 23. The disc-shaped impeller 21 is accommodated in the chamber 24 of the housing 20. More particularly, the disc-shaped impeller 21 is pivotally supported in the housing 20 for rotation in the chamber 24.

The housing 20 includes an upper housing 20a having the blood inlet port 22 and the blood outlet port 23 and a lower housing 20b, both formed from a non-magnetic material in a volute shape. The housing 20 defines therein the blood chamber 24 in fluid communication with the inlet and outlet ports 22 and 23. The impeller 21 is accommodated within the housing 20. The inlet port 22 protrudes from near the center of the upper surface of the housing 20 in a substantially vertical direction. The outlet port 23 projects from a side surface of the generally cylindrical housing 20 in a tangential direction.

The disc-shaped impeller 21 is accommodated within the blood chamber 24 of the housing 20. The impeller 21 includes a disc-shaped member or lower shroud 21a defining a lower surface, an annular plate-shaped member or upper shroud 21b defining an upper surface and opening at the center, to form a center opening 21c and a plurality of (six in the illustrated embodiment) vanes 18 formed between the lower and upper shrouds. The vanes 18 define a corresponding plurality of blood passages 26 between two adjacent ones and between the lower and upper shrouds, each blood passage being closed along lower and upper sides 26a, 26b thereof by portions of the lower and upper shrouds, respectively. Each blood passage 26 extends from the center opening to the outer periphery of the impeller 21 in a curved fashion. Differently stated, the vanes 18 are formed between adjacent blood passages 26. In the illustrated embodiment, the vanes 18 and blood passages 26 are respectively provided at equiangular intervals and to substantially the same shape. The cross-sectional area of blood passages 26 is substantially constant in a blood flow direction (the cross-sectional area being perpendicular to the flow direction). The substantially constant cross-sectional area of blood passages 26 in the flow direction is effective for protecting the blood flow against turbulence by a fluctuation of flow velocity, minimizing damage to blood. Alternatively, the cross-sectional area of blood passages 26 may decrease in a flow direction. With such outwardly convergent fluid passages, the fluid (blood) flow becomes an accelerating flow, also preventing the flow from turbulence.

The magnetic material 25 is embedded in the vane 18, so as to be completely enclosed by material of the vanes, as can be seen in FIG. 2 for example. The magnetic material is a permanent magnet and serves as a follower magnet. Preferably pieces of the magnetic material 25 are embedded in at least two vanes 18, especially in all the vanes 18 as best shown in FIG. 1. Embedment of the discrete magnetic pieces 25 in a plurality of vanes 18 ensures to realize a relatively compact impeller 21 because the impeller must be increased in size in order to accommodate a continuous magnetic ring. Embedment of such plural discrete magnetic pieces 25 also ensures magnetic coupling with the rotor 31 to be described later. Each magnetic piece 25 is preferably circular in horizontal cross section as seen from FIG. 1.

Further included in the impeller 21 is a shaft 46 which extends downward from the lower surface of the disc-shaped lower shroud at its center. The shaft 46 is supported for rotation by a ball bearing 47 mounted in a recess formed at the center of the lower housing 20b. With this bearing, the impeller 21 is supported for rotation within the housing 20. The ball bearing 47 is separated from the blood chamber 24 by a seal member 48. The seal member 48 prevents blood in the chamber 24 from penetrating into the recess of the lower housing 20b and hence, the ball bearing 47.

The magnetic pieces 25 are provided in order that the impeller 21 be attracted away from the blood inlet port 22 by permanent magnets 33 in the rotor 31 of the rotational torque generating section 3 to be described later and that the rotational torque be transmitted from the torque generating section 3 to the impeller 21.

The impeller rotation torque generating section 3 includes a housing 34, the rotor 31 accommodated in the housing 34, and a motor for rotating the rotor 31 (whose internal structure is not shown in FIG. 2). The rotor 31 includes a rotating disc 32 and a plurality of permanent magnets 33 disposed on one surface (or the fluid pump side) of the rotating disc 32. The rotor 31 at its center is fixedly secured to the rotating shaft of the motor (not shown). The plurality of permanent magnets 33 are equiangularly distributed in accordance with the magnetic pieces 25 of the impeller 21, that is, the number and location of permanent magnets 33 are coincident with the number and location of magnetic pieces 25 (which are also permanent magnets). Instead, an annular permanent magnet 33 may be used.

The impeller rotation torque generating section 3 is not limited to the illustrated one having the rotor and motor. For example, an arrangement of stator coils may be used as long as it can attract the magnetic pieces (of permanent magnets) 25 of the impeller 21 for driving the impeller for rotation.

In the illustrated embodiment, the blood pump unit 2 and the rotational torque generating unit 3 are removably joined. This leads to the advantage that even when the rotational torque generating unit tails during operation, only that unit can be replaced without a need for replacement of the entire blood pump assembly. The invention is not limited to the illustrated embodiment, and the blood pump unit 2 and the rotational torque generating unit 3 may be integrally joined (see FIG. 8).

Figure 3:
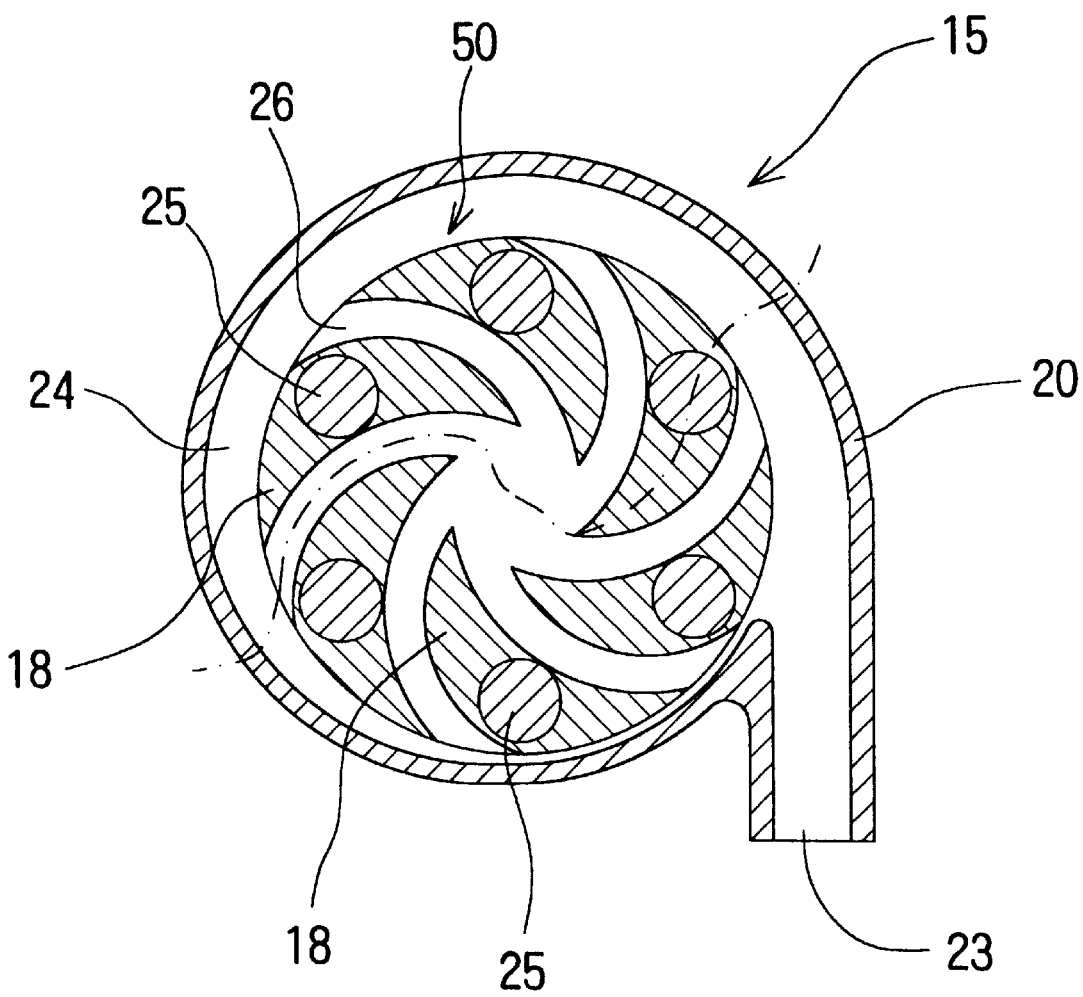
FIGS. 3 and 4 illustrate a centrifugal fluid pump assembly according to a second embodiment of the invention.
Figure 4:
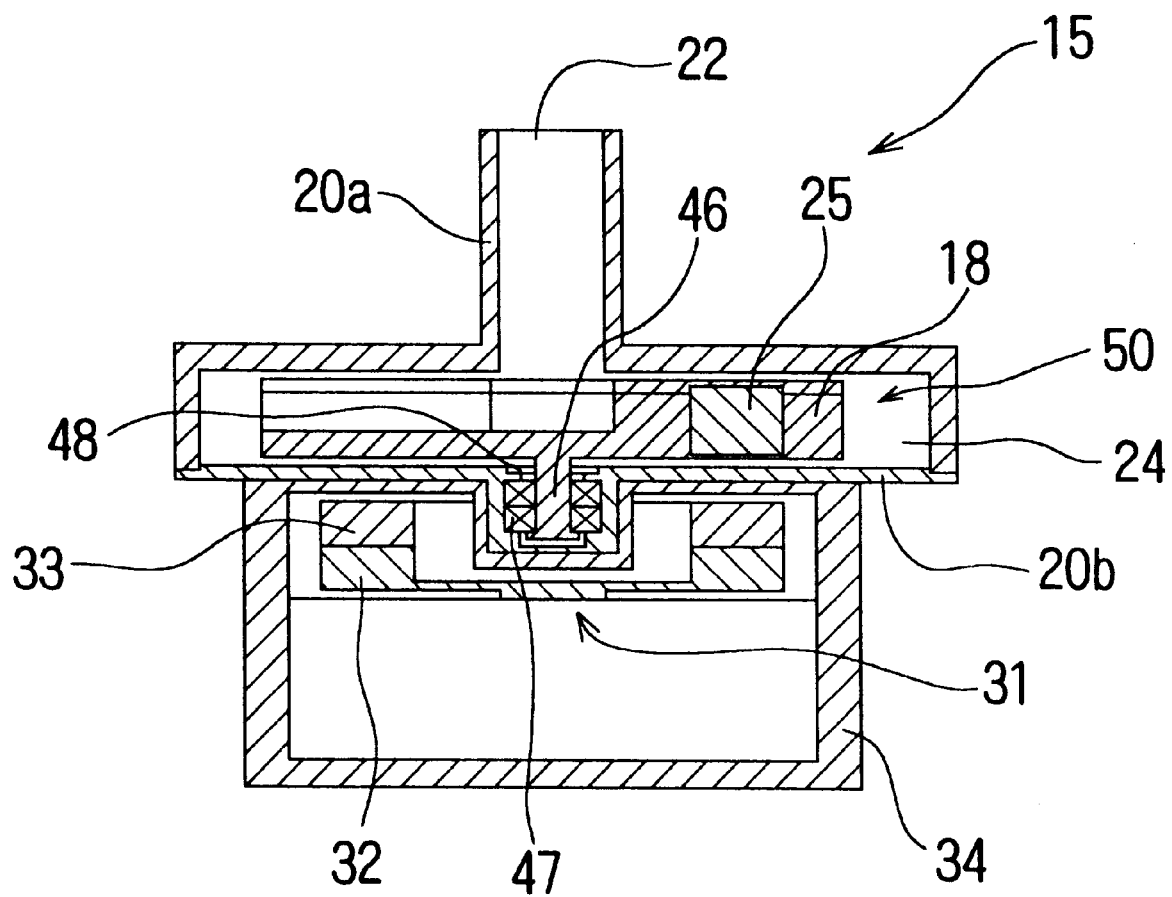

Next, the centrifugal blood pump assembly is described by referring to the second embodiment shown in FIGS. 3 and 4. The only difference between the blood pump assembly shown in FIGS. 3 and 4 and the assembly shown in FIGS. 1 and 2 resides in the shape of the impeller. The impeller 21 shown in FIGS. 1 and 2 is of the dosed type whereas the impeller 50 shown in FIGS. 3 and 4 are of the semi-open type. More particularly, the impeller 50 of the second embodiment is constructed by removing the upper shroud from the impeller 21 of the first embodiment. The blood passages 26 are defined by the vanes 18 as side surfaces and the lower shroud as the bottom while the upper side of the passages 26 is open to the blood chamber 24.

Figure 5:
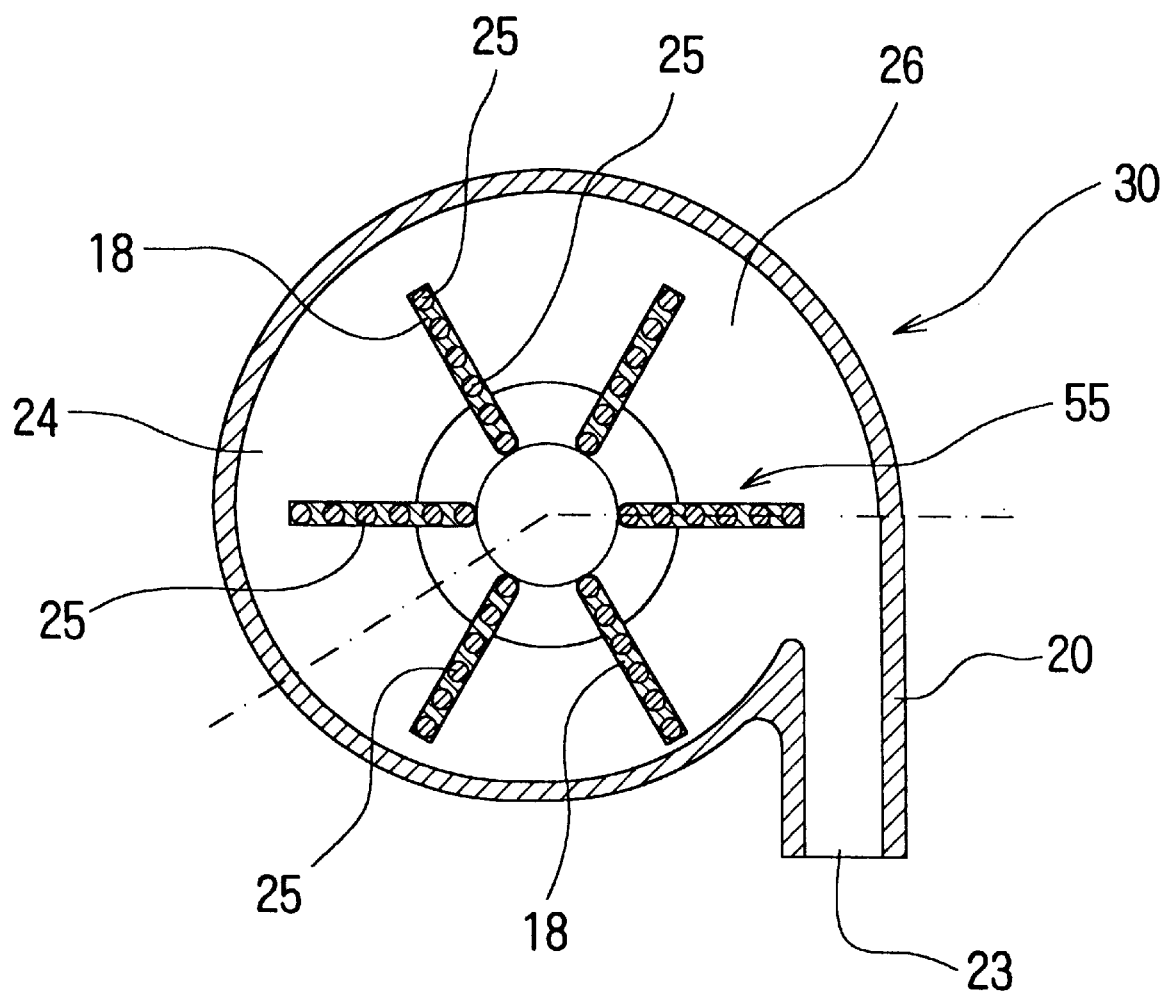
FIGS. 5 and 6 illustrate a centrifugal fluid pump assembly according to a third embodiment of the invention.
Figure 6:
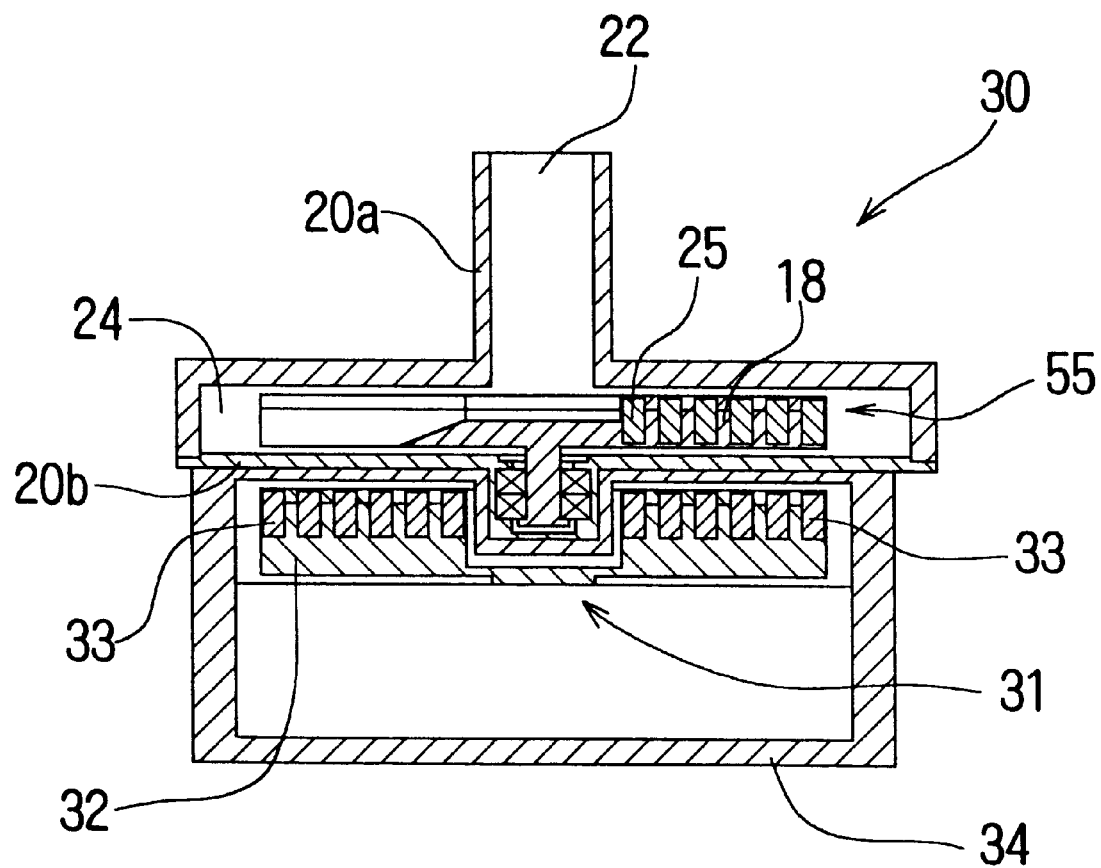

A further centrifugal blood pump assembly is described by referring to the third embodiment shown in FIGS. 5 and 6. The only difference between the blood pump assembly shown in FIGS. 5 and 6 and the assembly shown in FIGS. 1 and 2 resides in the shape of the impeller and rotor. The impeller 55 used in the third embodiment is of the open type in that the impeller has neither the upper shroud nor the lower shroud. The blood passages 26 are defined by the vanes 18 as side surfaces while the upper and lower sides of the passages 26 are open to the blood chamber 24. The plural vanes 18 are thin vanes of a fixed width (as viewed m FIG. 5) extending radially outward from the opening to the periphery of the impeller 55 in a substantially straight fashion. As a consequence, the blood passages 26 are fan shaped as viewed in FIG. 5. With this constructions the impeller 55 is reduced in height as a whole.

Since the magnetic pieces 25 which can be disposed in the thin vanes 18 must have a very small diameter, a plurality of tiny magnetic pieces 25 are radially arranged in each vane 18 to form a magnetically coupled row in order to provide a driving torque equivalent to the large magnets in the wide vanes 18 as in the first embodiment. Specifically, a plurality of magnetic pieces 25 (of permanent magnet) are linearly arranged and embedded in each vane 18. As viewed from the overall impeller, magnetic pieces 25 are positioned such that plural sets of equiangularly distributed magnetic pieces define a plurality of concentric circles. Differently stated, magnetic pieces 25 are distributed at equiangular intervals on a plurality of concentric circles about the central opening of the impeller. This impeller 55 has the advantage that its axial or vertical height can be reduced because the upper and lower shrouds are unnecessary, although a magnetic coupling force is somewhat reduced because the magnets which can be disposed in the vanes are significantly reduced in size.

A plurality of permanent magnets 33 are fixedly secured to the rotor 31 of the impeller rotation torque generating section in accordance with the distribution (number and location) of the magnetic pieces or permanent magnets 25 of the impeller 55.

Figure 7:
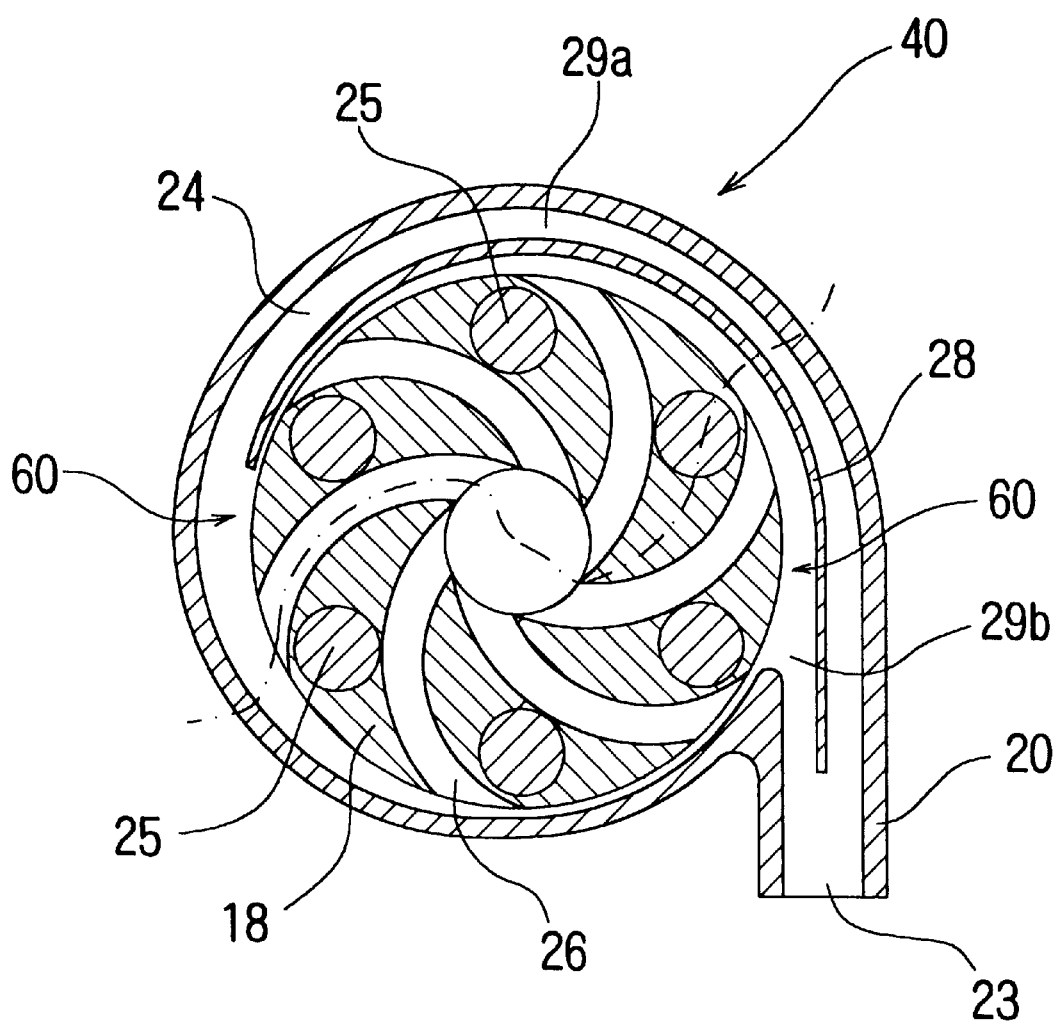
FIGS. 7 and 8 illustrate a centrifugal fluid pump assembly according to a fourth embodiment of the invention.
Figure 8:
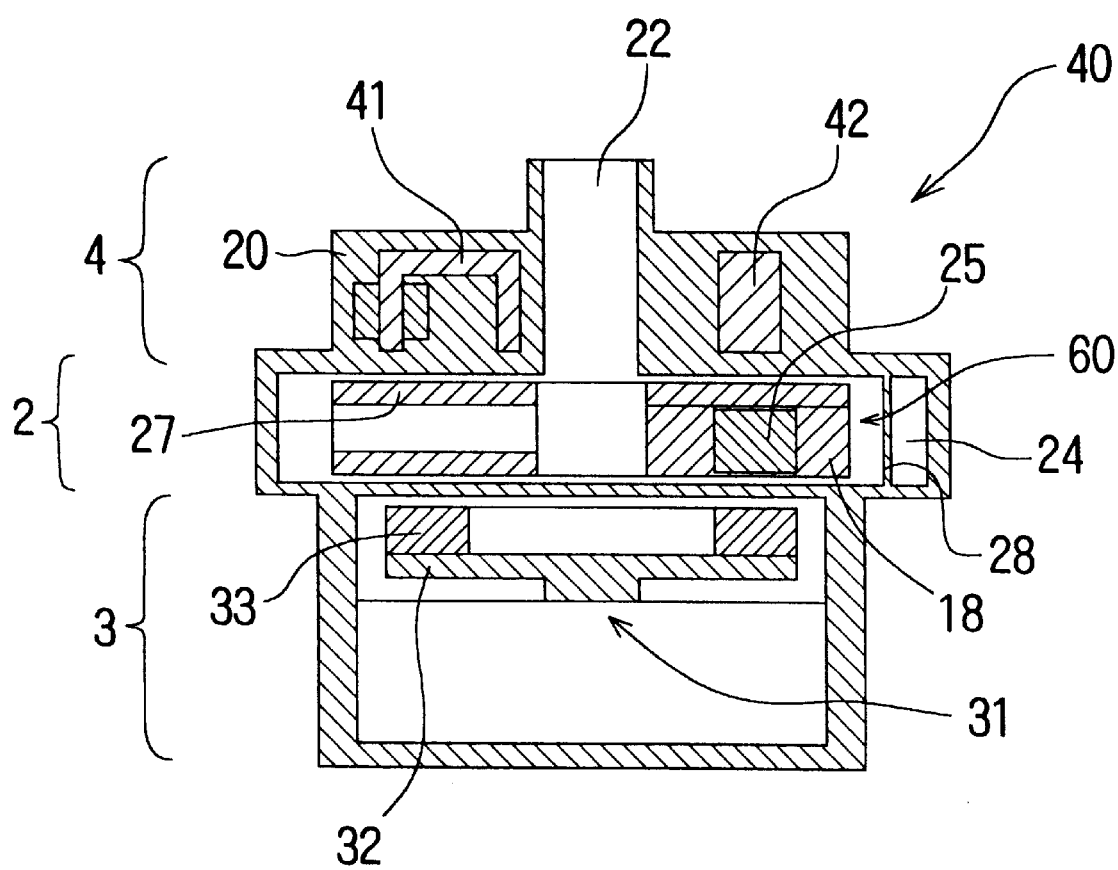

Referring to FIGS. 7 and 8, a centrifugal fluid pump assembly of the magnetic bearing type according to a fourth embodiment of the invention is described. FIG. 7 is a horizontal cross-sectional view of the impeller therein. FIG. 8 is a vertical cross-sectional view of the pump assembly while only the impeller is cut along a curved dot-and-dash line in FIG. 7.

This centrifugal fluid pump assembly 40 includes a centrifugal fluid pump 2 comprising a housing 20 having a blood inlet port (fluid inlet port) 22 and a blood outlet port (fluid outlet port) 23 and adapted to receive blood (fluid) therein, and an impeller 60 having magnetic pieces 25 disposed therein and accommodated for rotation in the housing 20 for feeding the blood (fluid) by a centrifugal force developed during rotating. Also included are an uncontrolled magnetic bearing means (or impeller rotation torque generating section) 3 for magnetically supporting the impeller 60, and a controlled magnetic bearing means (or impeller position control section) 4 for magnetically supporting the impeller 60. The uncontrolled magnetic bearing means 3 and controlled magnetic bearing means 4 cooperate such that the impeller 60 rotates while it is held in position within the housing 20.

As mentioned just above, the centrifugal fluid pump assembly 40 of this embodiment includes, the fluid pump section 2, rotational torque generating section 3, and impeller position control section 4.

Since the fluid pump assembly of the invention is typically applied as a blood pump, the following description refers to its embodiment as a blood pump.

The housing 20 has the blood inlet port 22 and the blood outlet port 23 and is formed from a non-magnetic material in a volute shape. The housing 20 defines therein the blood chamber 24 in fluid communication with the inlet and outlet ports 22 and 23. The impeller 60 is accommodated within the housing 20. The inlet port 22 protrudes from near the center of the upper surface of the housing 20 in a substantially vertical direction. The outlet port 23 projects from a side surface of the generally cylindrical housing 20 in a tangential direction.

The disc-shaped impeller 60 having a central through-hole is accommodated within the blood chamber 24 in the housing 20. The impeller 60 includes an annular lower shroud defining a lower surface and opening at the center, an annular upper shroud defining an upper surface and opening at the center, and a plurality of (six in the illustrated embodiment) vanes 18 formed between the lower and upper shrouds. The vanes 18 define a corresponding plurality of (six in the illustrated embodiment) blood passages 26 between two adjacent ones and between the lower and upper shrouds. Each blood passage 26 is contiguous to the central opening of the impeller 60 and extends from the center opening to the outer periphery of the impeller 60 in a curved fashion. Differently stated, the vanes 18 are formed between adjacent blood passages 26. In the illustrated embodiment, the vanes 18 and blood passages 26 are respectively provided at equiangular intervals and to substantially the same shape. The cross-sectional area of blood passages 26 is substantially constant in a blood flow direction (the cross-sectional area being perpendicular to the flow direction).

The magnetic material 25 is embedded in the vane 18. The magnetic material 25 is a permanent magnet and serves as a follower magnet. Pieces of magnetic material 25 are provided in order that the impeller 60 be attracted away from the blood inlet port 22 by a permanent magnet 33 in a rotor 31 of the rotational torque generating section 3 to be described later and that the rotational torque be transmitted from the torque generating section 3 to the impeller 60. Preferably the magnetic pieces 25 are embedded in at least two vanes 18, especially in all the vanes 18 as best shown in FIG. 7. Embedment of the discrete magnetic pieces 25 in a plurality of vanes 18 ensures to realize a relatively compact impeller 60 because the impeller must be increased in size in order to accommodate a continuous magnetic ring. Embedment of such plural discrete magnetic pieces 25 also ensures magnetic coupling with the rotor 31 to be described later. Each magnetic piece 25 is preferably circular in horizontal cross section as seen from FIG. 7.

The impeller 60 further includes a magnetic member 27 which itself constitutes an upper shroud or which is attached to an upper shroud. In the illustrated embodiment, the upper shroud in its entirety is constructed by the magnetic member 27. The magnetic member is provided in order that an electromagnet 41 of the impeller position control section 4 to be described later magnetically attract the impeller 60 toward the inlet port 22. The magnetic member may be formed of magnetic stainless steel, nickel or soft iron.

When a magnetically coupled centrifugal pump having a closed type impeller is manufactured by a prior art method, it is necessary to position a magnet within a lower shroud and join an upper shroud thereto. This necessitates a first division line for dividing the lower shroud and a second division line constituting a junction between the vane and the upper shroud. In contrast, the present invention which proposes to embed the magnetic material in the vanes of the impeller enables to manufacture a closed type impeller merely by setting only one division line intermediate the impeller vane or at the boundary between the vane and the upper shroud. This construction minimize the number of junctions and is effective for suppressing thrombus formation which is likely to occur at junctions.

Figure 9:
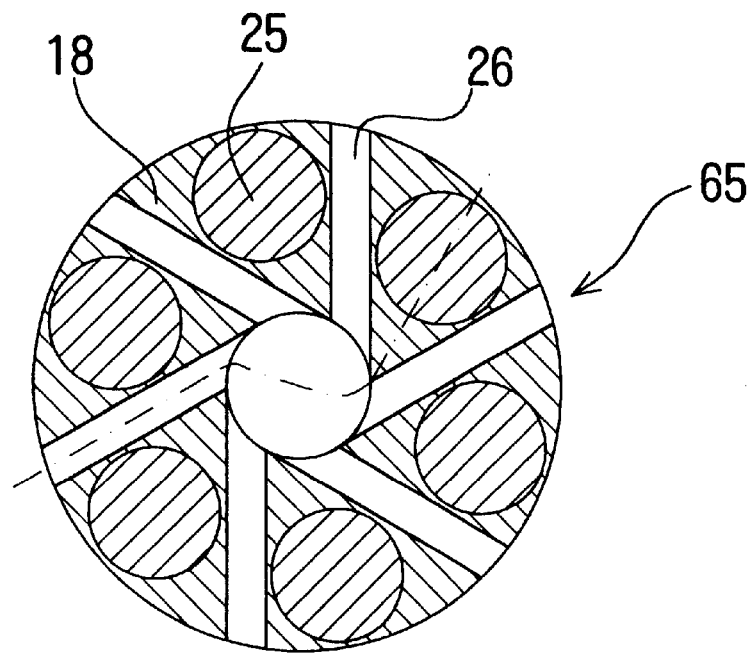
FIG. 9 is a horizontal cross-sectional view of an impeller used in a centrifugal fluid pump assembly according to a fifth embodiment of the invention.
Figure 10:
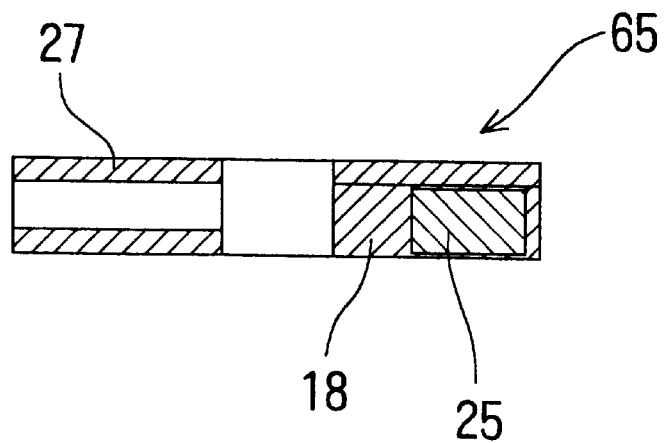
FIG. 10 is a vertical cross-sectional view of the impeller taken along a curved dot-and-dash line in FIG. 9.

The shape of the impeller is not limited to the illustrated one. Another impeller shape is shown in FIGS. 9 and 10 wherein the blood passages 26 are contiguous to the center opening of the impeller 65 and extend linearly from the center opening to the outer periphery of the impeller 65. In this impeller 65, the blood passages 26 are straight and have a substantially constant crossectional area transverse to a flow direction. Such straight blood passages 26 not only make it easy to machine and manufacture the impeller, but are also effective for suppressing turbulence to the blood flow by directional changes, eventually inhibiting damage to blood. In addition, the straight blood passages 26 allow magnetic pieces of greater size to be disposed in the vanes, ensuring a greater magnetic coupling force.

In the embodiment shown in FIGS. 7 and 8, a partition 28 which circumscribes the outer periphery of the impeller 60 over a half turn and extends into the blood outlet port 23 is provided in the blood chamber 24 of the housing 20 in proximity to its peripheral wall (exactly stated, in the space defined between the peripheral inner wall of the housing 20 and the peripheral edge of the impeller 60). The partition 28 divides the peripheral space of the blood chamber 24 of the housing 20 into two blood channels 29a and 29b whereby the blood forced by the impeller enters either of the channels 29a and 29b and the resulting two streams eventually merge at the outlet port 23. By dividing the peripheral space of the blood chamber 24 of the housing 20 into two blood channels 29a and 29b, a radial thrust which is otherwise created by an uneven radial pressure distribution in the housing 20 can be restrained. Then the uncontrolled magnetic bearing means becomes more stable.

The impeller position control section 4 and the rotational torque generating section 3 constitute a non-contact type magnetic bearing, which magnetically attracts the impeller 60 from opposite directions to steadily hold the impeller 60 at a proper position out of contact with the inner surface of the housing 20 so that the impeller 60 may rotate within the housing 20 without contacting its inner surface.

Included in the rotational torque generating section 3 are the housing 20, the rotor 31 accommodated in the housing 20, and a motor for rotating the rotor 31 (whose internal structure is not shown in FIG. 8). It is noted that the housing 20 in the embodiment of FIG. 8 is an integral housing serving as housings for all of sections 2, 3 and 4. The rotor 31 includes a rotating disc 32 and a plurality of permanent magnets 33 disposed on one surface (facing the fluid pump) of the rotating disc 32. The rotor 31 at its center is fixedly secured to the rotating shaft of the motor (not shown). The plurality of permanent magnets 33 are equiangularly distributed in accordance with the magnetic pieces 25 of the impeller 60, that is, the number and location of permanent magnets 33 are coincident with the number and location of magnetic pieces 25 (which are also permanent magnets).

Understandably, the impeller rotation torque generating section 3 is not limited to the illustrated one having the rotor and motor. For example, an arrangement of stator coils may be used as long as it can attract the magnetic pieces (of permanent magnets) 25 of the impeller 60 for driving the impeller for rotation.

Included in the impeller position control section 4 are a plurality of electromagnets 41 embedded in the housing 20 and a plurality of position sensors 42. In the impeller position control section 4, a plurality of (typically tree) electromagnets 41 and a plurality of (typically three) sensor 42 are respectively arranged at equiangular intervals while the angle between one electromagnet 41 and an adjacent sensor 42 is also equal. The electromagnet 41 consists essentially of a core and a coil. Three electromagnets 41 are arranged in the embodiment. More than three electromagnets, for example, four electromagnets may be arranged. By adjusting the electromagnetic forces of the electromagnets 41 in accordance with the results of detection of the position sensors 42 to be described later, forces acting on the impeller in a center a (z axis) direction can be balanced and moments about x and y axes perpendicular to the center axis (z axis) be equal.

The position sensor 42 detects the distance of a gap between the electromagnet 41 and the magnetic member 27 and produces an output of detection which is fed back to a control (not shown) for controlling electric current to the coil of the electromagnet 41. Even when a radial force as by gravity acts on the impeller 60, the impeller 60 is held at the center of the housing 20 by virtue of restoring forces of a magnetic flux between the permanent magnet 25 of the impeller 60 and the permanent magnet 33 of the rotor 31 and restoring forces of a magnetic flux between the electromagnet 41 and the magnetic member 27.

There has been described a centrifugal fluid pump assembly comprising a housing having an inlet port and an outlet port for fluid and adapted to receive fluid therein; an impeller having a magnetic material disposed therein and accommodated for rotation in the housing for feeding the fluid by a centrifugal force developed during rotation; and a rotational torque generating mechanism comprising a rotor having a magnet for attracting the magnetic material in the impeller and a motor for rotating the rotor, the rotational torque generating mechanism serving to impart a rotational torque to the impeller in a non-contact relationship for thereby rotating the impeller. The impeller has a plurality of vanes which define therebetween a corresponding plurality of fluid passages extending from the center to the outer periphery of the impeller. The magnetic material is disposed in the vane.

The centrifugal fluid pump assembly is defined in the second aspect as comprising a centrifugal fluid pump section comprising a housing having an inlet port and an outlet port for fluid and adapted to receive fluid therein and an impeller having a magnetic material disposed therein and accommodated for rotation in the housing for feeding the fluid by a centrifugal force developed during rotation; and a rotational torque generating section comprising a rotor having a magnet for attracting the magnetic material in the impeller and a motor for rotating the rotor, the rotational torque generating section serving to impart a rotational torque to the impeller in a non-contact relationship. The impeller has a plurality of vanes which define therebetween a corresponding plurality of fluid passages extending from the center to the outer periphery of the impeller. The magnetic material is disposed in the vane.

In a prior art centrifugal fluid pump, magnetic pieces (or driven magnets) are located in the lower shroud of the impeller. As a result, the axial eight of the impeller is increased by the distance of the magnets. In contrast, the centrifugal fluid pump of the invention is successful in reducing the axial height of the impeller because magnet pieces are located in the impeller vanes. As a result, the radially protected area of the impeller is reduced and hence, the radial trust developed by a radial imbalance of pressure distribution is restrained whereby the radial load applied to the bearing of the impeller is reduced, improving the bearing to be more durable. Since the impeller is reduced in height, the entire pump assembly is reduced in size and becomes easy to handle. The dead volume (priming volume ) of the pump is also reduced.

Further, there has been described a centrifugal fluid pump assembly comprising a centrifugal fluid pump comprising a housing having an inlet port and an outlet port for fluid and adapted to receive fluid therein and an impeller having a magnetic material disposed therein and accommodated for rotation in the housing for feeding the fluid by a centrifugal force developed during rotation; controlled magnetic bearing means for magnetically supporting the impeller; and uncontrolled magnetic bearing means for magnetically supporting the impeller, the uncontrolled magnetic bearing means comprising a rotor having a magnet for attracting the magnetic material in the impeller and a motor for rotating the rotor. The controlled magnetic bearing means and the uncontrolled magnetic bearing means cooperate such that the impeller rotates while it is held in position within the housing. The impeller has a plurality of vanes which define therebetween a corresponding plurality of fluid passages extending from the center to the outer periphery of the impeller. The magnetic material is disposed in the vane.

As mentioned above, in a prior art centrifugal fluid pump wherein magnets are located in the lower shroud of the impeller, the axial height of the impeller is increased by the distance of the magnets. In contrast, the centrifugal fluid pump of the invention is successful in reducing the axial height of the impeller because magnetic pieces are located in the impeller vanes. This reduces the radial thrust developed in the impeller, which in turn, reduces the load to the magnetic bearing used in the fluid pump, thereby ensuring to hold the impeller at a radial position in a more stable manner.

Although some preferred embodiments have been described, many modifications and variations may be made thereto in the light of the above teachings. It is therefore to be understood that within the scope of the appended claims, the invention may be practiced otherwise than as specifically described.

We claim:

1. A centrifugal blood pump assembly comprising:
   a generally cylindrical housing adapted to receive blood, said housing having a blood inlet port extending from near a center of an upper surface of the generally cylindrical housing in a substantially vertical direction and a blood outlet port projecting from a side surface of the generally cylindrical housing in a tangential direction,
   an impeller having pieces of magnetic material disposed therein and accommodated for rotation in said housing for feeding blood by a centrifugal force developed during rotation of the impeller, and
   a rotational torque generating mechanism comprising a rotor having a magnet for attracting the pieces of magnetic material in said impeller and a motor for rotating said rotor, said rotational torque generating mechanism serving to impart a rotational torque to said impeller in a non-contact relationship for thereby rotating said impeller,
   said impeller including a disc-shaped lower shroud defining a lower surface, and an annular plate-shaped upper shroud defining an upper surface, the impeller defining a center opening and including a plurality of vanes defining a corresponding plurality of blood passages disposed between adjacent vanes, said blood passages each extending from the center opening to an outer periphery of the impeller and being closed along upper and lower sides thereof by the upper and lower shrouds, respectively, each of at least two of the vanes forming a magnetic material store space, said pieces of magnetic material being embedded in respective ones of the at least two vanes and completely surrounded by the material of said vanes so that said pieces of magnetic material are not exposed at a surface of the impeller.

2. The centrifugal blood pump assembly of claim 1 wherein plural pieces of magnetic material are disposed in plural vanes.

3. The centrifugal blood pump assembly of claim 1 wherein the blood passages in said impeller have a cross-sectional area which is substantially constant or declining in a blood flow direction.

4. The centrifugal blood pump assembly of claim 1 wherein the blood passages in said impeller extend straight.

5. The centrifugal blood pump assembly of claim 1 wherein plural pieces of magnetic material are disposed in all vanes.

6. A centrifugal blood pump assembly comprising:

a centrifugal blood pump section comprising a generally cylindrical housing adapted to receive blood, said generally cylindrical housing having a blood inlet port extending from near a center of an upper surface of the generally cylindrical housing in a substantially vertical direction and a blood outlet port projecting from a side surface of the generally cylindrical housing in a tangential direction, and an impeller having pieces of magnetic material disposed therein and accommodated for rotation in said housing for feeding blood by a centrifugal force developed during rotation of the impeller, and a rotational torque generating section comprising a rotor having a magnet for attracting the magnetic material in said impeller and a motor for rotating said rotor, said rotational torque generating section serving to impart a rotational torque to said impeller in a non-contact relationship, said impeller including a disc-shaped lower shroud defining a lower surface, and an annular plate-shaped upper shroud defining an upper surface, the impeller defining a center opening and including a plurality of vanes defining a corresponding plurality of blood passages disposed between adjacent vanes, said blood passages each extending from the center opening to an outer periphery of the impeller and being closed along upper and lower sides thereof by the upper and lower shrouds, respectively, each of at least two of the vanes forming a magnetic material store space, said pieces of magnetic material being embedded in respective ones of the at least two vanes and completely surrounded by the material of said vanes, so that said pieces of magnetic material are not exposed at a surface of the impeller.

7. The centrifugal blood pump assembly of claim 6 wherein plural pieces of magnetic material are disposed in plural vanes.

8. The centrifugal blood pump assembly of claim 6 wherein the blood passages in said impeller have a cross-sectional area which is substantially constant or declining in a blood flow direction.

9. The centrifugal blood pump assembly of claim 6 wherein the blood passages in said impeller extend straight.

10. The centrifugal blood pump assembly of claim 6 wherein plural pieces of magnetic material are disposed in all vanes.

11. A centrifugal blood pump assembly comprising:

a centrifugal blood pump section comprising a generally cylindrical housing adapted to receive blood, said generally cylindrical housing having a blood inlet port extending from near a center of an upper surface of the generally cylindrical housing in a substantially vertical direction and a blood outlet port projecting from a side surface of the generally cylindrical housing in a tangential direction, and an impeller having pieces of magnetic material disposed therein and accommodated for rotation in said housing for feeding blood by a centrifugal force developed during rotation of the impeller, controlled magnetic bearing means for magnetically supporting the impeller, and uncontrolled magnetic bearing means for magnetically supporting the impeller, said uncontrolled magnetic bearing means comprising a rotor having a magnet for attracting the pieces of magnetic material in said impeller and a motor for rotating said rotor, said controlled magnetic bearing means and said uncontrolled magnetic bearing means cooperating such that the impeller rotates while it is held in position within the housing, said impeller including a disc-shaped lower shroud defining a lower surface, and an annular plate-shaped upper shroud defining an upper surface, the impeller defining a center opening and including a plurality of vanes defining a corresponding plurality of blood passages disposed between adjacent vanes, said blood passages each extending from the center opening to an outer periphery of the impeller and being closed along upper and lower sides thereof by the upper and lower shrouds, respectively, each of at least two of the vanes forming a magnetic material store space, said pieces of magnetic material being embedded in respective ones of the at least two vanes and completely surrounded by the material of said vanes, so that said pieces of magnetic material are not exposed at a surface of the impeller.

12. The centrifugal blood pump assembly of claim 11 wherein said impeller further includes a magnetic member for constituting a magnetic bearing with said controlled magnetic bearing means, and said controlled magnetic bearing means includes a fixed electromagnet for attracting the magnetic member of said impeller and a position sensor for detecting the position of the magnetic member of said impeller.

13. The centrifugal blood pump assembly of claim 11 wherein plural pieces of magnetic material are disposed in plural vanes.

14. The centrifugal blood pump assembly of claim 11 wherein the blood passages in said impeller have a cross-sectional area which is substantially constant or declining in a blood flow direction.

15. The centrifugal blood pump assembly of claim 11 wherein the blood passages in said impeller extend straight.

16. The centrifugal blood pump assembly of claim 11 wherein plural pieces of magnetic material are disposed in all vanes.

* * * * *

UNITED STATES PATENT AND TRADEMARK OFFICE
CERTIFICATE OF CORRECTION

PATENT NO. : 6,030,188
DATED : February 29, 2000
INVENTOR(S) : Toshihiko NOJIRI, et al.

It is certified that error appears in the above-indentified patent and that said Letters Patent is hereby corrected as shown below:

In column 4, line 51, delete "material" and insert --material 25--

In column 5, line 64, delete "m" and insert --in--.

In column 7, line 59, delete "minimize" and insert --minimizes--.

In column 8, line 58, delete "tree" and insert --three--.

In column 8, line 59, delete "sensor" and insert --sensors--.

Signed and Sealed this

Twenty-fourth Day of April, 2001

Attest:

NICHOLAS P. GODICI

Attesting Officer     Acting Director of the United States Patent and Trademark Office